(12) United States Patent
Chornovol et al.

(10) Patent No.: US 11,992,570 B2
(45) Date of Patent: May 28, 2024

(54) PORTABLE DISINFECTOR STERILIZING SPRAYER

(71) Applicant: Wi Labs IP Holding, LLC, Reno, NV (US)

(72) Inventors: Volodymyr Chornovol, Zhytomyr (UA); Oleksandr Yatsenko, Dnipro (UA)

(73) Assignee: Wi Labs IP Holding, LLC, Reno, NV (US)

( * ) Notice: Subject to any disclaimer, the term of this patent is extended or adjusted under 35 U.S.C. 154(b) by 399 days.

(21) Appl. No.: 17/079,488

(22) Filed: Oct. 25, 2020

(65) Prior Publication Data
US 2022/0031892 A1 Feb. 3, 2022

(51) Int. Cl.
*A61L 2/22* (2006.01)

(52) U.S. Cl.
CPC .............. *A61L 2/22* (2013.01); *A61L 2202/11* (2013.01); *A61L 2202/15* (2013.01); *A61L 2202/16* (2013.01)

(58) Field of Classification Search
CPC ..... A61L 2/22; A61L 2202/15; A61L 2202/16
See application file for complete search history.

(56) References Cited

U.S. PATENT DOCUMENTS

| RE26,012 E | * | 5/1966 | Green | F16K 31/58 |
| | | | | 222/402.18 |
| 5,927,548 A | * | 7/1999 | Villaveces | B05B 11/3001 |
| | | | | 222/325 |
| 9,913,561 B1 | * | 3/2018 | Rodriguez | A47K 10/32 |
| 10,464,736 B1 | * | 11/2019 | Pindor | B65D 83/303 |
| 2010/0155430 A1 | * | 6/2010 | Schwandt | B05B 15/30 |
| | | | | 222/383.3 |
| 2014/0061233 A1 | * | 3/2014 | Lang | B65D 51/00 |
| | | | | 220/203.23 |

* cited by examiner

*Primary Examiner* — Sean E Conley
*Assistant Examiner* — Justin Hwang
(74) *Attorney, Agent, or Firm* — Inventa Capital Group PLC

(57) ABSTRACT

A portable sterilizing sprayer includes a gripper shaped shell, and a nozzle on the front surface of the shell. The back part of the shell includes a clamping device which can be clamped on the waist belt. The inner part of the shell presents a cavity to hold a disinfectant solution. The front end of the shell is provided with a pressing part for pressing the thumb, and when the pressing part is pressed, the disinfection in the liquid storage cavity is carried out. When it is used, it does not need to be removed, and the palm is pressed near the thumb and pressed with the thumb. The disinfecting liquid can be sprayed on the palm of the palm and can be sterilized at any time, so the portable disinfector is convenient to carry and to use it at any time.

18 Claims, 4 Drawing Sheets

A-A

PORTABLE DISINFECTOR STERILIZING SPRAYER

FIELD OF THE INVENTION

The invention relates to the technical field of sterilizing sprayers, and more specifically, to a portable disinfector sprayer.

BRIEF DESCRIPTION OF THE INVENTION

Today all countries in the world are threatened by the spread of new, deadly, and contagious diseases, such as coronavirus (COVID19), or the possibility of terrorist attacks with biological weapons. Travelers may spread dangerous microbes intentionally or unintentionally as there are many epidemic prone viruses around the world. To avoid contact infection by hand, people need to wash their hands regularly or when they cannot wash their hands, they disinfect their hands by spraying some disinfectants. This often requires the use of hand washing disinfectant spray containers.

The existing disinfectant spray container for hand washing is usually filled with a disinfectant solution in a cylindrical container, and a pressure sprayer is installed at the upper opening of the container. However, because of its large volume and inconvenient use, this cylindrical disinfectant spray container can only be placed in a fixed location and is not convenient to carry around. Therefore, when people go out, they cannot disinfect their opponents at any time, which brings inconvenience to people and increases the chance of virus infection.

The aim of the invention is to provide a portable disinfector sprayer which is convenient to carry and convenient to use to overcome the shortcomings of the above technology.

SUMMARY OF THE INVENTION

A portable sterilizing sprayer includes a housing having a front surface, a back surface and an inner cavity at least partially enclosed by the front and back surfaces. The inner cavity includes a first chamber configured to be selectively filled with a liquid to be stored therein and a second chamber separated from the first chamber by a partitioning wall. A nozzle is configured to spray or dispense the liquid stored in the first chamber. A trigger assembly includes a sleeve disposed at and forming an upper portion of the housing and an actuating manifold movably disposed within the second chamber. The sleeve is connected to the actuating manifold.

A clamping member is disposed at the back surface of the housing and is configured for attachment to an article worn by a user. The actuating manifold, in response to a force applied to the sleeve, is configured to move from a rest position into a pressed position causing the nozzle to spray or dispense the liquid stored in the first chamber wherein the actuating manifold, in response to the force removed from the sleeve, is configured to return to the rest position.

An advantage of the present invention is to provide a hand-held sanitizer to hold a solution to be sprayed from the nozzle to the palm of the hand, and offer a unique shape that is designed to be hand held and small in size and can be clipped on the waist belt when going out.

Another advantage of the present invention is to provide the hand held sanitizer having a soft rubber sleeve, a button and a button cavity, the button cavity is arranged in the shell, a partition board is arranged between the button cavity and the liquid storage cavity, the button is arranged in the button cavity, the soft rubber sleeve is fixed at the front end of the shell, and the inner side of the soft rubber sleeve is connected with the button.

Still another advantage of the present invention is to provide the hand held sanitizer with the liquid storage cavity provided with a suction pipe, the tail section of the suction pipe extends to the button cavity and is fixed on the partition board.

Still another advantage of the present invention is to provide the hand held sanitizer with the connection between the shell and the soft rubber sleeve is provided with a number of convex pillars, the two sides of the soft rubber sleeve are provided with a number of fixed through holes, the convex pillars are sheathed in the fixed through holes, the two sides of the button are provided with long strip-shaped limit through holes, one of the convex pillars is threaded in the limit through-hole.

Still another advantage of the present invention is to provide the hand held sanitizer wherein the inner wall of the button cavity is located at the nozzle and is provided with a fixed seat, and the nozzle is installed and fixed in the fixed seat.

Still another advantage of the present invention is to provide the hand held sanitizer wherein the back wall of the shell is provided with a liquid injection hole for adding disinfection solution, and the liquid injection hole is provided with a cover plug.

Still another advantage of the present invention is to provide the hand held sanitizer wherein the cover plug includes an integrally formed hole plug and a flat cover, and the housing is located next to the liquid injection hole and is internally provided with a groove to accommodate the cover.

The beneficial effect of the invention is as follows: the portable disinfector sprayer of the present disclosure is designed to be hand-held and small in size and can be clipped on the waist belt when going out. When it is used, it does not need to be removed. It can be actuated with the palm of the hand by pressing the button on the front end with the thumb, so that the disinfectant liquid can be sprayed in the palm of the hand that can be sterilized at any time. The disinfectant sprayer is easy to carry and can be conveniently used at any time.

The objects and advantages of the present invention will be more readily apparent from inspection of the following specification, taken in connection with the accompanying drawing, wherein like numerals refer to like parts throughout and in which an embodiment of the present invention is described and illustrated.

The exact manner in which the foregoing and other objects and advantages of the invention are achieved in practice will become more clearly apparent when reference is made to the following detailed description of the preferred embodiments of the invention described in detail in the following specification and shown in the accompanying drawings, where in like reference numbers indicate corresponding parts throughout.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
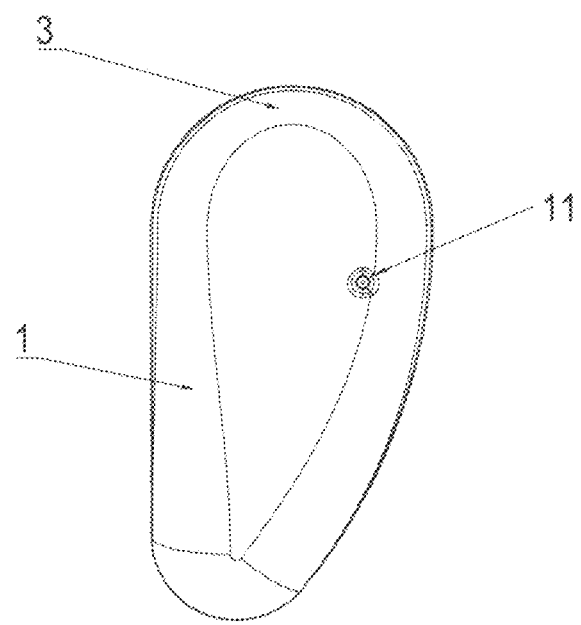
FIG. 1 illustrates a side view of a portable disinfector sprayer.
Figure 2:
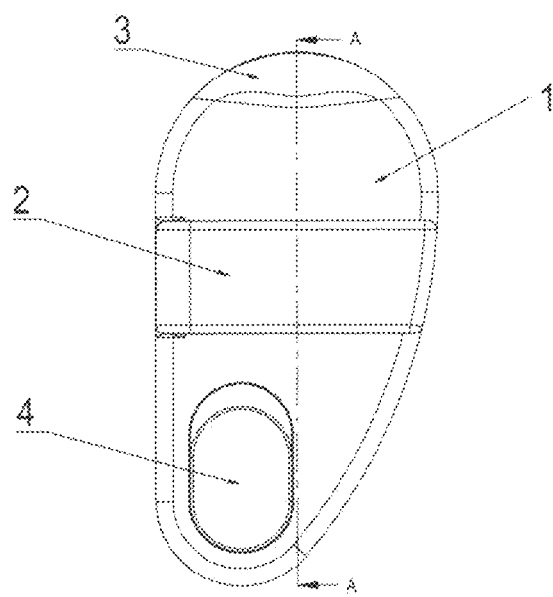
FIG. 2 is a rear view of the portable disinfector sprayer.
Figure 3:
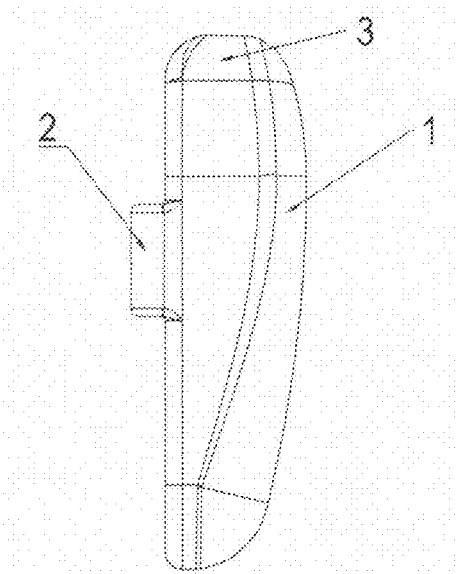
FIG. 3 is a top view of the portable disinfectant sprayer.

Referring to the Figures, a portable sterilizing or disinfectant sprayer is shown at 1. As used herein, the singular forms "a," "an," and "the" include plural referents unless the context clearly dictates otherwise. Thus, for example, the term "module" is intended to mean one or more modules or a combination of modules. Furthermore, as used herein, the term "based on" includes based at least in part on. Thus, a feature that is described as based on some cause, can be based only on that cause, or based on that cause and on one or more other causes.

It will be apparent that multiple embodiments of this disclosure may be practiced without some or all of these specific details. In other instances, well-known process operations have not been described in detail in order not to unnecessarily obscure the present embodiments. The following description of embodiments includes references to the accompanying drawing. The drawing shows illustrations in accordance with example embodiments. These example embodiments, which are also referred to herein as "examples," are described in enough detail to enable those skilled in the art to practice the present subject matter. The embodiments can be combined, other embodiments can be utilized, or structural, logical and operational changes can be made without departing from the scope of what is claimed. The following detailed description is, therefore, not to be taken in a limiting sense, and the scope is defined by the appended claims and their equivalents.

Alluding to the above, for purposes of this patent document, the terms "or" and "and" shall mean "and/or" unless stated otherwise or clearly intended otherwise by the context of their use. The term "a" shall mean "one or more" unless stated otherwise or where the use of "one or more" is clearly inappropriate. The terms "comprise," "comprising," "include," and "including" are interchangeable and not intended to be limiting. For example, the term "including" shall be interpreted to mean "including, but not limited to." In order to make the purpose, technical scheme and advantages of the invention clearer and clearer, the present invention is further described in detail in combination with the attached drawings and embodiments.

Referring to FIGS. 1 through 11, a portable sterilizing sprayer includes a housing 1 having a front surface 14, a back surface 15, and an inner cavity 10 at least partially enclosed by the front 14 and back 15 surfaces. The inner cavity 10 further extends to a first chamber configured to be selectively filled with a liquid to be stored therein and a second chamber 30 separated from the first chamber 10 by a partitioning wall 13.

A nozzle 11 is configured to spray or dispense the liquid stored in the first chamber 10. A trigger assembly includes a sleeve 31 disposed at and forming an upper portion of the housing 1 and an actuating manifold 32 movably disposed within the second chamber 30. The sleeve 31 is connected to the actuating manifold 32. A clamping member 2 is disposed at the back surface 15 of the housing 1 and is configured for attachment to an article worn by a user. The actuating manifold 32, in response to a force applied to the sleeve 31, is configured to move from a rest position into a pressed position causing the nozzle 11 to spray or dispense the liquid stored in the first chamber 10 wherein the actuating manifold 32, in response to the force removed from the sleeve 31, is configured to return to the rest position.

The actuating manifold 32 includes a piston chamber 320 extending along a linear direction of travel of the actuating manifold 32 and a discharge conduit 321 connected in fluid communication with and perpendicularly extending from the piston chamber 320. As can be best seen in FIGS. 6 and 7, the actuating manifold has an internal cavity 33 therein. The piston chamber 320 and the discharge conduit 321 are both entirely disposed within the internal cavity 33 of the actuating manifold 32. The internal cavity 33 is separated into two sub-cavities by a partitioning wall 34 and the piston chamber 320 positioned between the two sub-cavities and being supported on both sides by the partitioning wall 34. A suction pipe assembly 5 extends from the first chamber 10 into the second chamber 30 through an opening fitted with a sealing ring 53 in the partitioning wall 13. The suction pipe assembly 5 includes a tail tube portion 51 disposed at one end of the suction pipe assembly 5. An elbow tube portion 9 is disposed at an opposing end of the suction pipe assembly 5. A suction pipe portion SA is disposed there between.

The tail tube portion 51 is disposed entirely within the second chamber 30 and the elbow tube portion 9 is disposed entirely within the first chamber 10. The tail tube portion 51 of the suction pipe assembly 5 is securely connected in fluid communication with the piston chamber 320. A dispensing nozzle assembly 6 is disposed within the second chamber 30. The dispensing nozzle assembly 6 includes a nozzle member 61 and a connecting pipe 7 extending therefrom. The nozzle member 61 is connected in fluid communication, via the connecting pipe 7, with the discharge conduit 321 of the actuating manifold 32.

The nozzle member 61 is press-fitted into a fixed seat 18 connected to an interior side of the front surface 14 and is disposed within the second chamber 30, such that the nozzle member 61 is generally aligned with the nozzle 11. The liquid, in response to the actuating manifold 32 moved from the rest position into the pressed position, is extruded from the first chamber 10, via the connecting pipe 7, to the nozzle member 61 and is ejected from the nozzle member 61 through the nozzle 11. One end of the connecting pipe 7 is removably secured to the discharge conduit 321 by a clamp 8, and wherein another end of the connecting pipe 7 is removably secured to the nozzle member 61 by another clamp 8.

The back surface 15 includes a liquid injection aperture 12 for selectively adding the liquid into the first chamber 10 and a cover 4 for plugging or covering the liquid injection aperture 12. At least an upper surface of the sleeve 31 includes a soft rubber material. The sleeve 31 is fixedly secured to an inner side of the front surface 14 of the housing 1. The upper portion of the sleeve 31 is fabricated from a soft material such as, for example silicon. A rigid section 309 extends from the upper portion of the sleeve 31 and includes a number of fixed through holes 310.

Alluding to the above, in another embodiment of the present invention, the portable disinfector sprayer comprises a gripper shaped shell 1, namely, the housing 1 can be held in the hand, and the front face of the shell 1 is provided with a nozzle 11, and the nozzle 11 is relatively small. The back of the shell 1 is provided with a clamping member 2, one end of the clamping part 2 is fixed on one side of the shell, and the other end is an opening, and the clamping piece 2 can be clamped on the waist belt through the opening, so that the spray container is easy to carry. In this embodiment, the shell 1 is enclosed by an outer shell 14 and an inner shell 15. The inner part of the shell 1 is provided with a liquid storage cavity 10 which can fill the disinfectant solution.

The front end of the outer shell 1 is provided with a pressing part 3 on the upper part, and the pressing part 3 is convenient for pressing with the thumb when holding the spray container. When the pressing part 3 is pressed by the thumb, the disinfectant solution in the liquid storage chamber 10 can be sprayed into the palm of the hand in the form of mist or fluid from the nozzle 11. The back of the shell 1 is also provided with a liquid injection hole 12 for adding disinfectant solution. The liquid injection hole 12 is provided with a cover plug 4.

The cover plug 4 includes an integrally formed hole plug 41 and a flat cover 42. The shell 1 is located next to the liquid injection hole 12 and is internally provided with a groove 120 to accommodate the cover 42. The hole plug 41 is used to block the injection hole 12 after the injection to prevent the liquid from leaking out. The hole plug 41 is provided with a cover 42, which is convenient for pulling out the hole plug 41 and opening the liquid injection hole 12 by lifting the cover 42 by hand when adding liquid.

Figure 4:
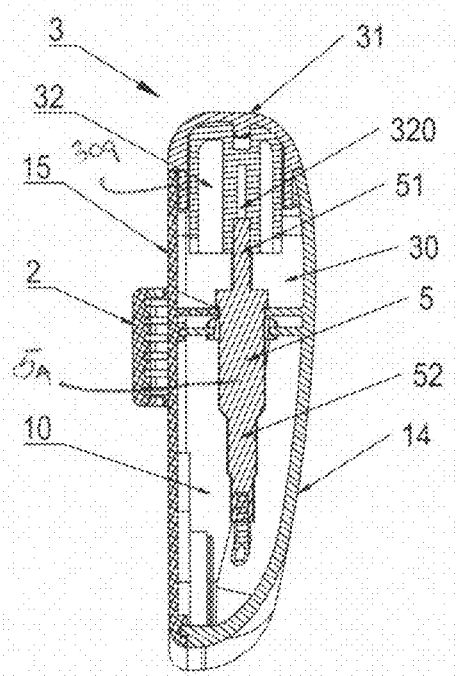
FIG. 4 is a cross sectional view of the portable disinfector sprayer.
Figure 5:
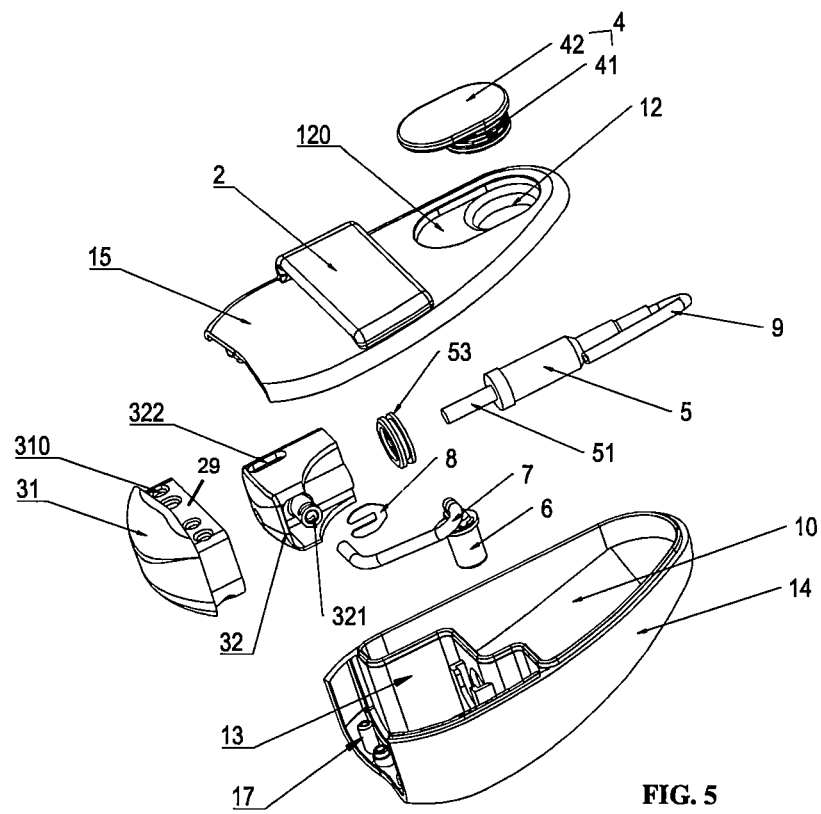
FIG. 5 is an exploded view of the portable disinfector sprayer.

As shown in FIGS. 4 and 5, the pressing part 3 includes a soft rubber sleeve 31, a button 32 and a button cavity 30 for accommodating the button 32. The soft rubber sleeve 31 is made of soft colloid. The button cavity 30 is arranged in the shell 1, a partition plate 13 is arranged between the button cavity 30 and the liquid storage cavity 10, the button 32 is arranged in the button cavity 30, the soft rubber sleeve 31 is fixed at the front end of the shell 1, and the inner side of the soft rubber sleeve 31 is connected with the button 32. The soft rubber sleeve 31 has certain elasticity. When the soft rubber sleeve 31 is pressed by hand, the button 32 is pressed at the same time. When the soft rubber sleeve 31 is relaxed, the soft rubber sleeve 31 returns to reset, and the button 32 is driven to return to reset.

As shown in FIGS. 4 through 8, a suction pipe 5 is arranged in the liquid storage cavity 10, and the tail section 51 of the suction pipe 5 extends into the button cavity 30 and is fixed on the partition plate 13. A check valve (not shown in the figure) is arranged inside the front section 52 of the suction pipe 5 to prevent the solution in the suction pipe from flowing backward when the button 32 is pressed. A sealing ring 53 is arranged at the joint between the tail section 51 of the suction pipe and the baffle plate 13, and the sealing ring 53 is used to prevent the liquid in the liquid storage cavity 10 from leaking through the connection.

The inner part of the button 32 is provided with a piston chamber 320 which can accommodate the tail section 51 of the suction pipe along the pressing direction, and the piston cavity 320 is set on the tail section 51 of the suction pipe, which can make axial reciprocating motion on the tail section 51 of the suction pipe. The bottom of the piston chamber 320 is perpendicular to the piston chamber 320 and is provided with a discharge pipe 321 connected with it. The inner side of the nozzle 11 is provided with a nozzle 6. The nozzle 61 of the nozzle 6 is directly opposite to the nozzle 11, and a nozzle 7 is connected between the discharge pipe 321 and the nozzle 6.

The principle of the spray is that when the press is pressed by hand, 31, the button 32 is pressed at the same time, the button moves towards the front 51 of the straw 5, the inner cavity space formed by the piston chamber 320 and the tail section 51 of the straw is compressed, and the volume decreases. The tail section 51 is a part of the mechanism of sprayer and it goes inside of the part 5 and compress internal volume of liquid that caused the liquid go through the tail section 51 to outside. When the button 32 is pressed the liquid is already inside of the part 5 wherein the compression forces the liquid to go out. The back section of the straw 5 has a check valve to prevent the solution from being reversed, so that the liquid in the piston chamber 320 is extruded and discharged to the discharge pipe 321. The liquid is extruded into the nozzle 6 through the nozzle 7, and further, the liquid is ejected through the nozzle 61 in the nozzle 6 and ejected through the nozzle 11, and the liquid is atomized due to pressure extrusion.

When the thumb is pressed when the rubber sleeve is relaxed, the rubber sleeve 31 is reset back and forth, and the button 32 is also reset. The volume of the inner cavity space formed by the piston cavity 320 and the tail section 51 of the straw is increased, forming a certain vacuum, causing suction in the straw 5 to suck and suck the liquid. When the housing is filled first time its needs to be pumped several times to start working and only one push is required moving forward to spray the liquid out. in the liquid storage chamber 10 and accumulate in the 320 of the plug chamber.

Alluding to the above, the portable disinfector sprayer of this embodiment is designed to be hand-held and small in size and can be clamped on the waist belt by clamping 2 when going out. When the utility model is not used, the palm is close to the sprayer and the thumb press the pressing part 3, so that the disinfectant solution in the liquid storage chamber 10 can be sprayed on the palm of the hand and can be sterilized at any time. Therefore, the portable disinfector sprayer is convenient to carry and can be conveniently used at any time.

As shown in FIGS. 5 through 8, a clip 8 is removably arranged at the joint of the discharge pipe 321 and the connecting pipe 7 and the joint of the dispensing nozzle assembly 6 and the connecting pipe 7, and the clamp 8 is used to fix the connecting pipe 7. A clamping groove 3210 is arranged on the discharge pipe 321. The clamping groove 3210 can accommodate the clip 8, which can clamp and fix the connecting pipe 7 in the clamping groove 3210, so that when the solution in the discharge pipe 321 is extruded the connecting pipe 7 will not fall off due to the exerted pressure or force. Similarly, the dispensing nozzle assembly 6 has the same clamping groove (not shown) and clamping structure, so that the connecting pipe 7 will not accidentally lose its connection to the dispensing nozzle assembly 6.

Figure 9:
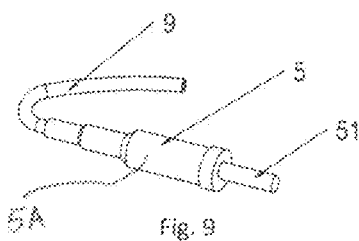
FIG. 9 is a perspective view of a pipette and elbow portion of the portable disinfector sprayer.
Figure 10:
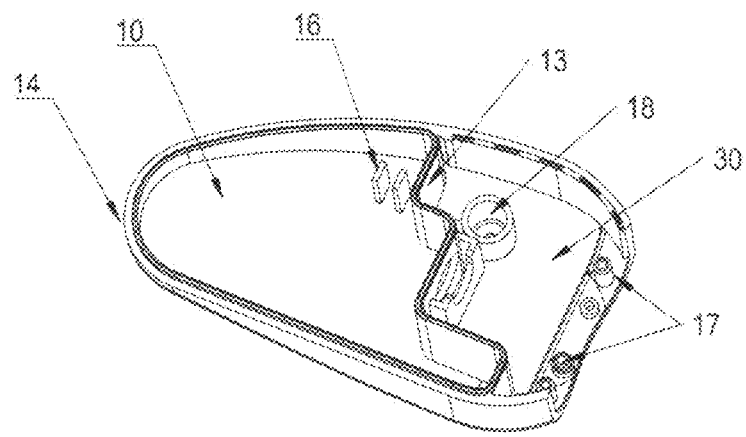
FIG. 10 is a perspective view of an outer shell of the portable disinfector sprayer.

As shown in FIGS. 9 and 10, the front section 52 of the suction pipe is connected with an elbow 9, and the suction end of the elbow 9 is arranged at the bottom of the liquid storage chamber 10. In this way, when the liquid in the liquid storage chamber 10 is less, the liquid will accumulate at the bottom of the liquid storage cavity 10, so that the suction end of the elbow 9 can still inhale liquid and deliver it to the suction pipe 5. The inner wall of the liquid storage chamber 10 is located at the suction end of the elbow 9, and is provided with a fixing plate 16, which is used to fix the suction end of the elbow 9, so as to ensure that the suction end of the elbow 9 is fixed at the bottom of the liquid storage chamber 10, so that the liquid in the liquid storage cavity 10 can continue to be inhaled after the liquid in the liquid storage cavity 10 is reduced.

Figure 6:
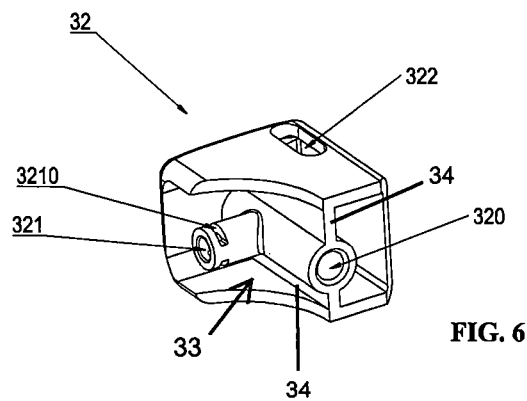
FIG. 6 is a perspective view of a button portion of the portable disinfector sprayer.
Figure 7:
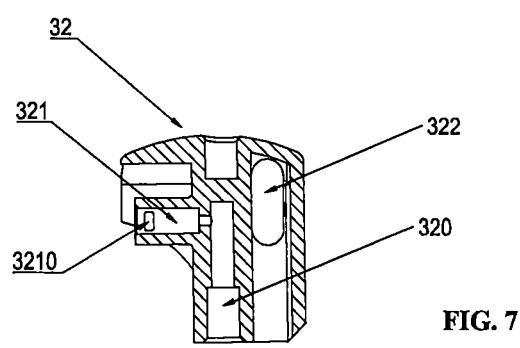
FIG. 7 is a cross sectional view of the button portion of the portable disinfector sprayer.
Figure 8:
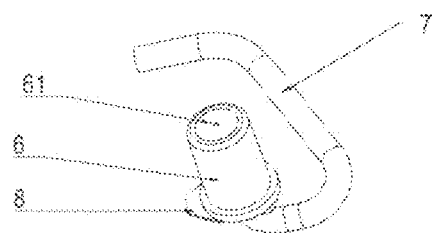
FIG. 8 is a perspective view of a nozzle portion of the portable disinfector sprayer.
Figure 11:
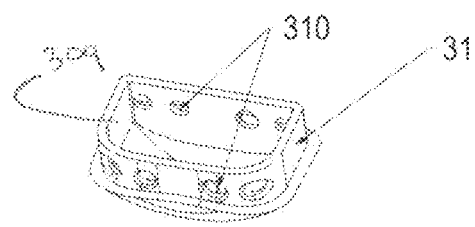
FIG. 11 is a perspective view of a flexible rubber sleeve of the portable disinfector sprayer.

As shown in FIGS. 10 and 11, the connection of the housing 1 and the soft rubber sleeve 31 is provided with a number of convex pillars 17 that are fixedly arranged on an inner side of at least the front surface 14 of the housing 1, as shown in FIGS. 5 and 10. A pair of opposing sidewalls 29 of the soft rubber sleeve 31 are provided with a number of fixed through holes 310, and the convex pillars 17 are sheathed in the fixed through holes 310, so that the soft rubber sleeve 31 is fixedly connected to the housing 1. The two opposing sides of the actuating manifold 32, as shown in FIGS. 5-7, are provided with a long strip-shaped limit through hole 322. One of the convex pillars 17 is threaded in the limit through-hole 322. The actuating manifold 32 can only move back and forth in the limit through hole 322 due to the limitation of the convex pillar 17. In this way, the movement direction of the actuating manifold 32 cannot be dislocated, which may result in an uneven stress and subsequently deformation of the tail tube portion 51 of the suction pipe 5.

As shown in FIG. 10, the inner wall of the button chamber 30 is provided with a fixed seat 18 at the nozzle 11, and the spray head 6 is fixed in the fixed seat 18, so that the nozzle 6 cannot fall off or deviate when the spray force is applied, so that the nozzle 61 cannot be accurately aligned with the nozzle 11.

The above description is only a better embodiment of the invention, and the above specific embodiment is not a limitation of the invention. Within the scope of the technical idea of the invention, various deformations and modifications can occur. All the embellishments, modifications or equivalent substitutions made by ordinary technicians in the art according to the above description belong to the scope of protection of the invention.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A portable sterilizing sprayer comprising:
   a housing having a front surface, a back surface and an inner cavity at least partially enclosed by said front and back surfaces, wherein said inner cavity comprises a first chamber configured to be selectively filled with a liquid to be stored therein and a second chamber separated from said first chamber by a partitioning wall;
   a nozzle configured to spray or dispense the liquid stored in said first chamber;
   a trigger assembly comprising (i) a sleeve disposed at and forming an upper portion of said housing and (ii) an actuating manifold movably disposed within said second chamber and having an internal cavity, said actuating manifold comprising a piston chamber and a discharge conduit both entirely disposed within said internal cavity of said actuating manifold, said discharge conduit is connected in fluid communication with and perpendicularly extending from said piston chamber, wherein said sleeve is connected to said actuating manifold;
   a dispensing nozzle assembly disposed within said second chamber, said dispensing nozzle assembly comprising a nozzle member and a connecting pipe extending therefrom, wherein said nozzle member is directly connected with said nozzle, and wherein said connecting pipe is directly connected with said discharge conduit of said actuating manifold; and
   wherein said actuating manifold, in response to a force applied to said sleeve, is configured to move from a rest position into a pressed position causing said nozzle to spray or dispense the liquid stored in said first chamber, and wherein said actuating manifold, in response to the force removed from said sleeve, is configured to return to the rest position, and
   wherein said sleeve has a pair of opposing sidewalls each including one or more fixed through holes, wherein an inner side of at least said front surface of said housing includes one or more convex pillars, and wherein said housing is connected with said sleeve by said one or more convex pillars being inserted into said one or more fixed through holes of said sleeve.

2. The portable sterilizing sprayer of claim 1, wherein said piston chamber extends along a linear direction of travel of said actuating manifold.

3. The portable sterilizing sprayer of claim 2 further comprising a suction pipe assembly extending from said first chamber into said second chamber through an opening fitted with a sealing ring in said partitioning wall.

4. The portable sterilizing sprayer of claim 3, wherein said suction pipe assembly comprises a tail tube portion disposed at one end of said suction pipe assembly, an elbow tube portion disposed at an opposing end of said suction pipe assembly, and a suction pipe portion disposed therebetween.

5. The portable sterilizing sprayer of claim 4, wherein said tail tube portion is disposed entirely within said second chamber and said elbow tube portion is disposed entirely within said first chamber.

6. The portable sterilizing sprayer of claim 4, wherein said tail tube portion of said suction pipe assembly is securely connected in fluid communication with said piston chamber.

7. The portable sterilizing sprayer of claim 1, wherein said nozzle member is press-fitted into a fixed seat connected to an interior side of said front surface and disposed within said second chamber, such that said nozzle member is generally aligned with said nozzle.

8. The portable sterilizing sprayer of claim 7, wherein the liquid, in response to said actuating manifold being moved from the rest position into the pressed position, is extruded from said first chamber, via said connecting pipe, to said nozzle member and is ejected from said nozzle member through said nozzle.

9. The portable sterilizing sprayer of claim 7, wherein one end of said connecting pipe is removably secured to said discharge conduit by a clamp, and wherein another end of said connecting pipe is removably secured to said nozzle member by another clamp.

10. The portable sterilizing sprayer of claim 1, wherein said back surface comprises a liquid injection aperture for selectively adding the liquid into said first chamber and a cover for plugging or covering said liquid injection aperture.

11. The portable sterilizing sprayer of claim 1, wherein at least an upper surface of said sleeve comprises a soft rubber material.

12. The portable sterilizing sprayer of claim 1, wherein said sleeve is fixedly secured to an inner side of said front surface of said housing.

13. A portable sterilizing sprayer comprising:
a housing having a front surface, a back surface and an inner cavity at least partially enclosed by said front and back surfaces, wherein said inner cavity comprises a first chamber configured to be selectively filled with a liquid to be stored therein and a second chamber separated from said first chamber by a partitioning wall;
a nozzle configured to spray or dispense the liquid stored in said first chamber;
an actuating manifold movably disposed within said second chamber and having an internal cavity, said actuating manifold comprising a piston chamber and a discharge conduit both entirely disposed within said internal cavity of said actuating manifold, said discharge conduit is connected in fluid communication with and perpendicularly extending from said piston chamber;
a dispensing nozzle assembly disposed within said second chamber, said dispensing nozzle assembly comprising a nozzle member and a connecting pipe extending therefrom, wherein said nozzle member is directly connected with said nozzle, and wherein said connecting pipe is directly connected with said discharge conduit of said actuating manifold; and
a clamping arm disposed at said back surface of said housing and configured for attachment to an article worn by a user;
wherein said actuating manifold, in response to a force applied thereto, is configured to move from a rest position into a pressed position causing said nozzle to spray or dispense the liquid stored in said first chamber, and wherein said actuating manifold, in response to the force removed therefrom, is configured to return to the rest position, and
a sleeve disposed at an upper portion of said housing, wherein said sleeve is connected to said actuating manifold such that said actuating manifold is configured to be actuated responsive to a force applied to said sleeve, said sleeve has a pair of opposing sidewalls each including one or more fixed through holes, wherein an inner side of at least said front surface of said housing includes one or more convex pillars, and wherein said housing is connected with said sleeve by said one or more convex pillars being inserted into said one or more fixed through holes of said sleeve.

14. The portable sterilizing sprayer of claim 13, wherein said nozzle member is press-fitted into a fixed seat connected to an interior side of said front surface and disposed within said second chamber, and wherein said nozzle member is generally aligned with said nozzle.

15. The portable sterilizing sprayer of claim 13 further comprising a suction pipe assembly extending from said first chamber into said second chamber through an opening in said partitioning wall.

16. The portable sterilizing sprayer of claim 15, wherein said suction pipe assembly comprises a tail tube portion disposed at one end of said suction pipe assembly, an elbow tube portion disposed at an opposing end of said suction pipe assembly, and a suction pipe portion disposed therebetween.

17. The portable sterilizing sprayer of claim 16, wherein said tail tube portion is disposed entirely within said second chamber and said elbow tube portion is disposed entirely within said first chamber.

18. The portable sterilizing sprayer of claim 16, wherein said tail tube portion of said suction pipe assembly is securely connected in fluid communication with said piston chamber of said actuating manifold.

* * * * *